United States Patent [19]

Masuda

[11] Patent Number: 5,621,969
[45] Date of Patent: Apr. 22, 1997

[54] METHOD OF FABRICATING ROLLER THERAPEUTIC APPLIANCE

[75] Inventor: Isamu Masuda, Fukuoka, Japan

[73] Assignee: Nihon Kenko Zoushin Kenkyukai Corporation, Fukuoka, Japan

[21] Appl. No.: 532,913

[22] Filed: Sep. 22, 1995

Related U.S. Application Data

[62] Division of Ser. No. 367,638, Jan. 3, 1995.

[30] Foreign Application Priority Data

Dec. 15, 1994 [JP] Japan ..................... 6-333963

[51] Int. Cl.⁶ ..................... B23P 15/00
[52] U.S. Cl. ..................... 29/895.21; 29/895.31; 492/13; 492/8
[58] Field of Search ..................... 492/8, 13; 29/895.3, 29/895.32, 895.21; 600/9, 15; 601/118, 123, 15, 18, 19

[56] References Cited

U.S. PATENT DOCUMENTS

| | | | |
|---|---|---|---|
| 2,628,611 | 2/1953 | Wagner | 492/13 |
| 3,149,403 | 9/1964 | Aurich et al. | 492/8 |
| 4,640,808 | 2/1987 | Okumura et al. | 492/8 |
| 5,384,957 | 1/1995 | Mohri et al. | 492/8 |

*Primary Examiner*—Irene Cuda
*Attorney, Agent, or Firm*—Jordan and Hamburg

[57] ABSTRACT

This invention relates to a roller therapeutic appliance and the method of fabricating it.

This invention is a roller therapeutic appliance in which a pressure roller composed of elastic material is rotatably disposed in a center portion of an operational axis having grips at both ends, and characterized in that an annular magnetic field generating source is embedded along an outer periphery of the pressure roller, which contacts with a human body.

According to the invention, the pressure roller is applied and rotated with pressure on a diseased part of the patient, then, not only pressing force due to the pressure roller but also a magnetic field due to the magnetic field generating source embedded in the pressure roller act on the diseased part, thereby both a massaging effect and a magnetic therapeutic effect can be obtained. Moreover, the annular magnetic field generating source can easily be embedded in a predetermined depth in a predetermined positions and can not be exposed from the surface of the pressure roller.

1 Claim, 9 Drawing Sheets

METHOD OF FABRICATING ROLLER THERAPEUTIC APPLIANCE

This is a division of application Ser. No. 08/367,638, filed Jan. 3, 1995.

TECHNICAL FIELD

This invention relates to a roller therapeutic appliance which performs massage and magnetic therapy by applying and rotating a pressure roller, supported on an operation axis, on the diseased part of the patient's body and to the method of fabricating it.

BACKGROUND ART

Conventionally, there is a roller therapeutic appliance having a structure that a pressure roller composed of elastic material like rubber is rotatably disposed via bearings in a center portion of an operation axis provided with grips at both ends. When this roller therapeutic appliance is used, a patient himself or another person grasps the grips at both ends of the operation axis, applies pressure with the pressure roller and rotates the pressure roller on a diseased part of the patient's body.

However, the roller therapeutic appliance of this type can give only a massaging effect that softens muscles externally by pressing force, and thus there was a problem that the appliance can give only a meager therapeutic effect.

Now, when a magnetic field is externally applied to a human body, the circulation of the blood becomes excellent and stiffness is alleviated, and these magnetic therapeutic effects are widely appreciated.

Then, a roller therapeutic appliance has been tried to fabricate which can give not only a massaging effect but also a magnetic therapeutic effect by embedding a plurality of permanent magnets along an outer peripheral surface of the pressure roller.

However, it is difficult to embed a permanent magnet at a predetermined depth into a predetermined position, because the pressure roller of the roller therapeutic appliance is made up by molding elastic material such as rubber, so there is a problem of a high rate of occurrence of defectives that a part of the permanent magnet is exposed from the surface of the pressure roller.

OBJECTS OF THE INVENTION

The object of the present invention is to provide a roller therapeutic appliance of easy-fabrication and an excellent therapeutic effect by embedding an annular magnetic field generating source into the pressure roller to generate the magnetic field.

DISCLOSURE OF INVENTION

This invention is a roller therapeutic appliance in which a pressure roller composed of elastic material is rotatably disposed in a center portion of an operational axis having grips at both ends, and characterized in that an annular magnetic field generating source is embedded along an outer periphery of the pressure roller, which contacts with a human body.

According to the invention, the roller therapeutic appliance is grasped with the grips at both ends of the operation axis, and the pressure roller is applied and rotated with pressure on a diseased part of the patient, then, not only pressing force due to the pressure roller but also a magnetic field due to the magnetic field generating source embedded in the pressure roller act on the diseased part, thereby both a massaging effect and a magnetic therapeutic effect can be obtained. Moreover, it is the annular magnetic field generating source that are embedded along the outer periphery of the pressure roller, so the parts for generating the magnetic field can easily be embedded in a predetermined depth in a predetermined positions and can not be exposed from the surface of the pressure roller.

In a preferable embodiment, the pressure roller has a constricted part in the center portion and the magnetic field generating sources are embedded in both sides interposing the constricted part. When said pressure roller is pressed on the back of a human body, the constricted part is just positioned above the spine of the body, and pressure and a magnetic field can be exerted on muscles on both sides of the spine.

In another embodiment of the pressure roller, the roller is disk-shaped and said annular magnetic field generating source is embedded along the outer periphery of the roller. In this case, the outer peripheral surface of the disk-shaped pressure roller contacts with the human body, so pressing force and a magnetic field act on one portion of the human body. Therefore said pressure roller is suitable for massage and magnetic therapy for legs or the like.

Moreover, if a configuration of providing a plurality of small protrusions at regular intervals along the periphery of the pressure roller, which contacts with a human body is added to either of the above embodiments, a diseased part can be locally pressed and stimulated by these small protrusions.

Preferably, said magnetic field generating source is configured by embedding a plurality of permanent magnets, at regular intervals, in a peripheral portion of a non-magnetic metal ring. This configuration facilitates the fabrication of the magnetic field generating source and eliminates fear of falling of the permanent magnets even when repeatedly used.

Instead of the above configuration, if an annular permanent magnet magnetized along the outer periphery of the ring is used as a magnetic field generating source, the fabrication cost of the field generating source becomes low.

The invention according to claim 7 is the method of fabricating a roller therapeutic appliance, and serially performs the following steps:

- a step in which a rod-shaped jig is inserted into an inner hole of an annular magnetic field generating source and the annular magnetic field generating source is supported on this jig;
- a step in which the annular magnetic field generating source supported on the jig and elastic material are introduced between molds and pressurized in a state of heat application, thereby a pressure roller embedding said magnetic field generating source is molded;
- a step in which the jig is pulled out from the molded pressure roller; and
- a step in which bearings are fitted into the inner hole of the pressure roller, and an operation axis is inserted into the bearings, thereby the pressure roller is rotatably supported at the center portion of the operation axis.

According to the above-mentioned method of fabricating the roller therapeutic appliance, the annular magnetic field generating source is supported on the rod-shaped jig, and then, said annular magnetic field generating source on the rod-shaped jig and rubber material are introduced between an upper die and a lower die and pressed, as a result, the pressure roller is molded with the magnetic field generating source embedded. So the magnetic field generating source can be, easily and correctly, positioned and embedded, and this facilitates the fabrication of the roller therapeutic appliance, as well as eliminates the fear of the occurrence of defectives due to exposure of the magnetic field generating source.

BEST MODE FOR CARRYING OUT THE INVENTION

Figure 1:
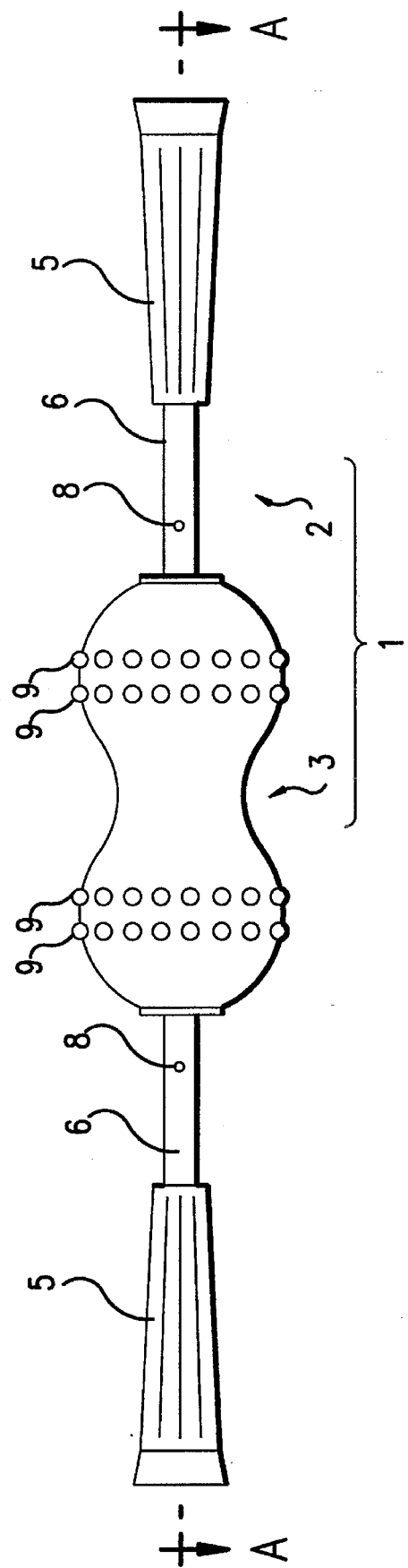
FIG. 1 is a front view showing an appearance of a roller therapeutic appliance of the first embodiment of the present invention.

FIG. 1 shows an appearance of a roller therapeutic appliance of the first embodiment of the present invention.

Figure 2:
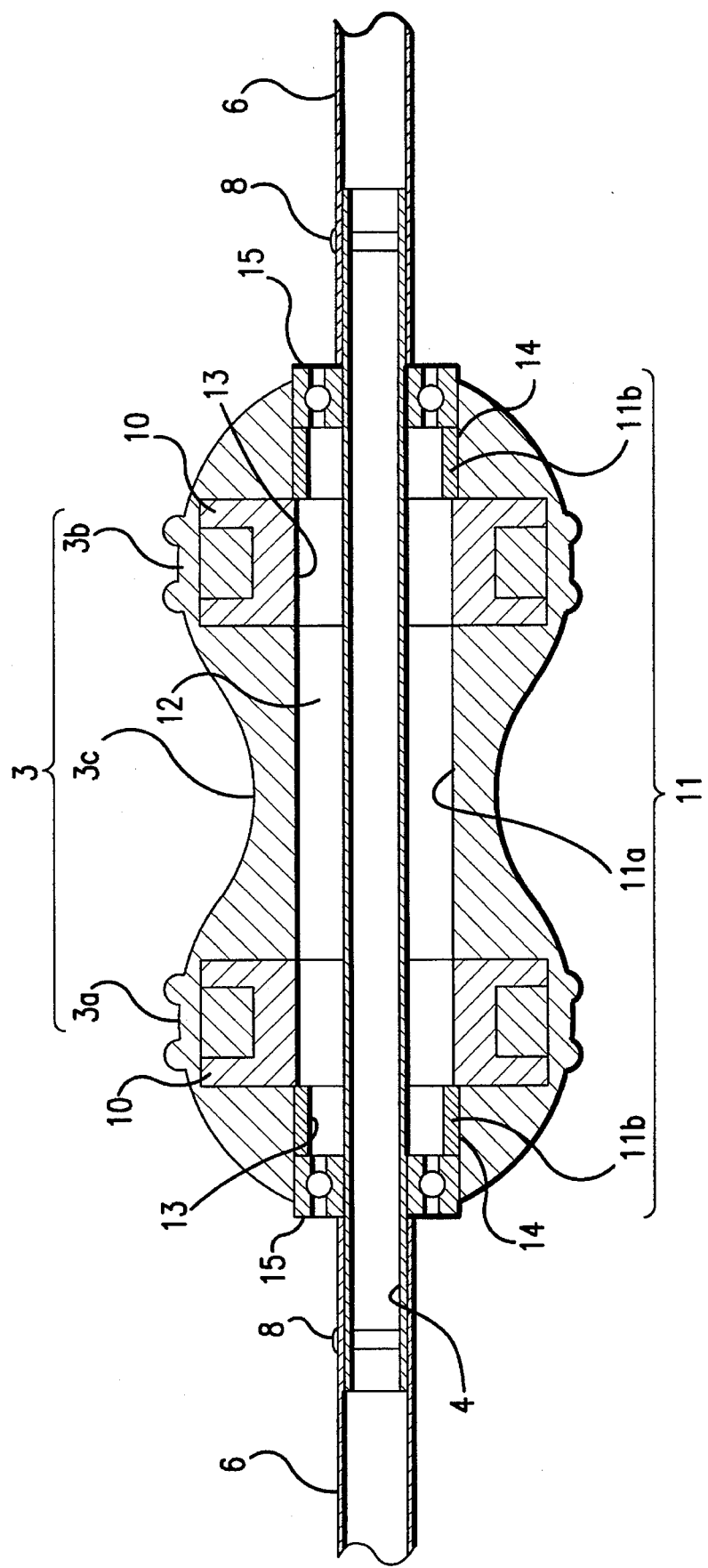
FIG. 2 is a sectional view taken in the line A—A of FIG. 1.

The roller therapeutic appliance 1 is comprised of an operation axis 2 and a pressure roller 3 rotatably disposed in the center of the operation axis 2, said operation axis 2, as shown in FIG. 2, is comprised of a central metal rod 4 supporting the pressure roller 3 and metal pipes 6, 6 which are fitted to the both ends of the metal rod 4 and fixed by rivets 8,8. An outer end of each metal pipe 6 is covered with a soft rubber grip 5.

Said metal rod 4 is somewhat longer than the pressure roller 3, and portions, of the metal rod 4, projecting from the both ends of the pressure roller 3 are fitted into said metal pipes 6, 6.

Figure 3:
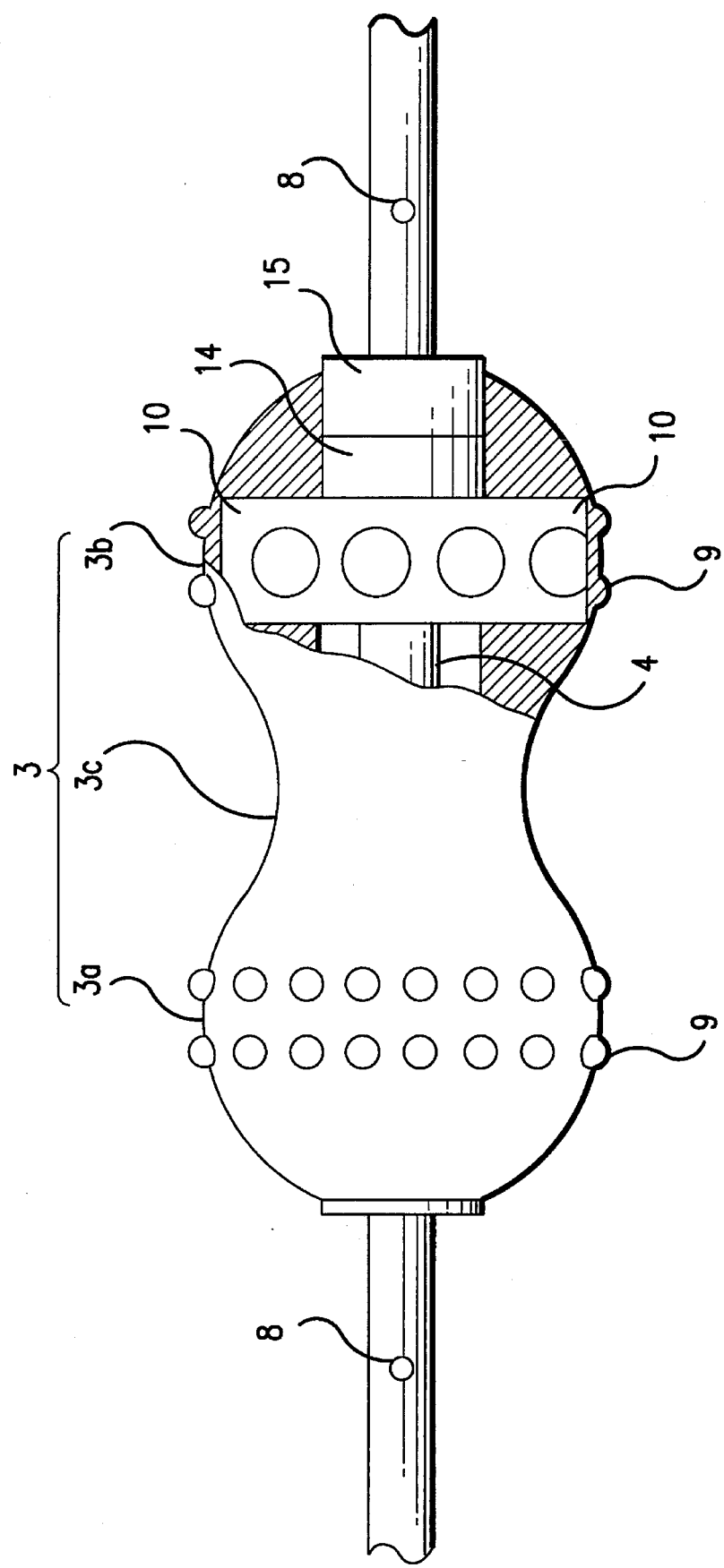
FIG. 3 is a partially broken front view showing the pressure roller.

Said pressure roller 3 is composed of elastic material such as soft rubber and integrally configured of a pair of sphere-shaped bodies 3a, 3b interposing a central constricted, part 3c. Each sphere-shaped bodies 3a, 3b, is integrally equipped with semi-spheric small protrusions 9 in two rows, at regular intervals on the peripheral surfaces, with the maximum diameter, which contacts with a human body. In each sphere-shaped bodies 3a, 3b, as shown in FIG. 2 and FIG. 3, annular magnetic field generating sources 10, 10 are embedded below the rows of the small protrusions 9. A hollow hole 11 with an inner diameter sufficiently larger than the diameter of the metal rod 4 of said operation axis 2 longitudinally penetrates into the pressure roller 3. The hollow hole 11 is comprised of a central portion 11a and end portions 11b, 11b, at both ends, having a diameter slightly larger than that of the central portion 11a. In both end portions of the central portion 11a, the magnetic field generating sources 10, 10 are positioned. In addition, the inner diameter of the central portion 11a conforms to the inner, diameter of an inner hole 13 of the magnetic field generating source 10.

The operation axis 2 is inserted into the hollow hole 11 of the pressure roller 3 and into the inner holes 13 of the magnetic field generating sources 10, and the pressure roller 3 is positioned on the metal rod 4 of the operation axis 2. Bearings 15, 15 and non-skid rings 14, 14 are tightly fitted to the respective end portions 11b, 11b of the hollow hole 11, and the pressure roller 3 is rotatably supported on the metal rod 4 via the bearings 15, 15. Between the inner peripheral surface of the pressure roller 3 and the metal rod 4 of the operation axis 2, a hollow space 12 is formed due to the central portion 11a of the hollow hole 11, and makes the deformation of the pressure roller 3 during use of the roller therapeutic appliance possible.

The non-skid ring 14 is made of synthetic resin and prevents the bearing 15 from shifting toward the central portion 11a of the hollow hole 11.

An outer portion of the bearing 15 is blocked by the non-skid ring 14 and an inner portion of it is blocked by an end face of the metal pipe 6 respectively, thus the bearing 15 is prevented from position shifting.

Figure 4:
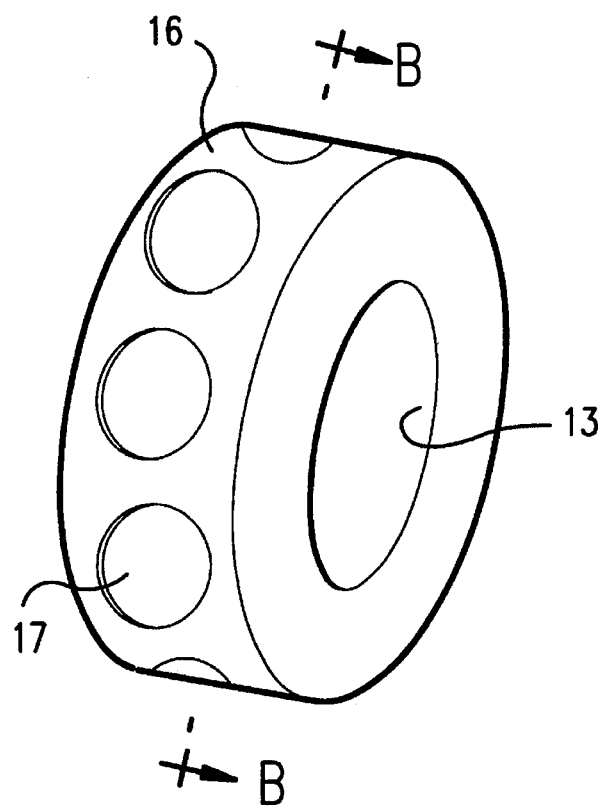
FIG. 4 is a perspective view showing an appearance of the magnetic field generating source.
Figure 5:
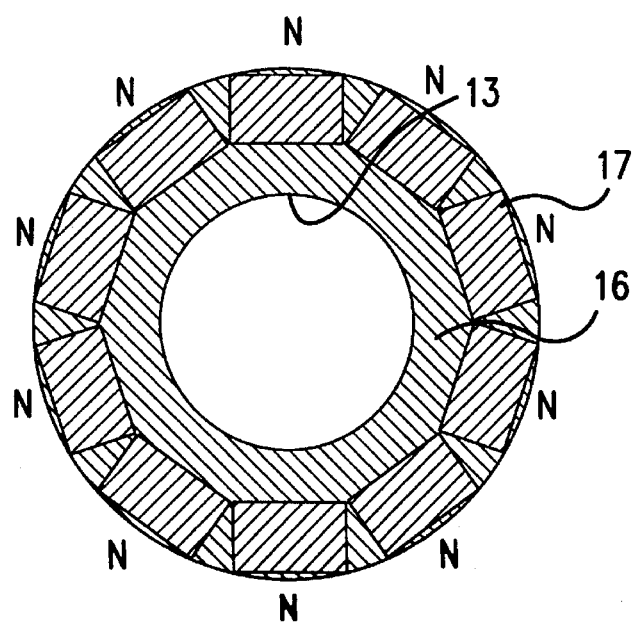
FIG. 5 is a sectional view taken in the line B—B FIG. 4.

FIG. 4 and FIG. 5 show a configuration of the magnetic field generating source 10.

The magnetic field generating source 10 is configured by that on an outer peripheral surface of an annular metal ring 16 composed of non-magnetic material such as aluminum, a plurality of mounting holes are provided at regular intervals, and cylindrical permanent magnet 17 is embedded in each mounting hole. Said metal ring 16 has nearly the same thickness as the width of the rows of the small protrusions 9 respectively provided on the sphere-shaped bodies 3a, 3b and has a smaller outer diameters than the maximum diameter of the sphere-shaped bodies 3a, 3b.

The permanent magnets 17 are embedded in the metal ring 16, with their N-poles directing outward, however they may be embedded in the metal ring 16, with their N-poles and S-poles alternately directing outward.

Figure 6:
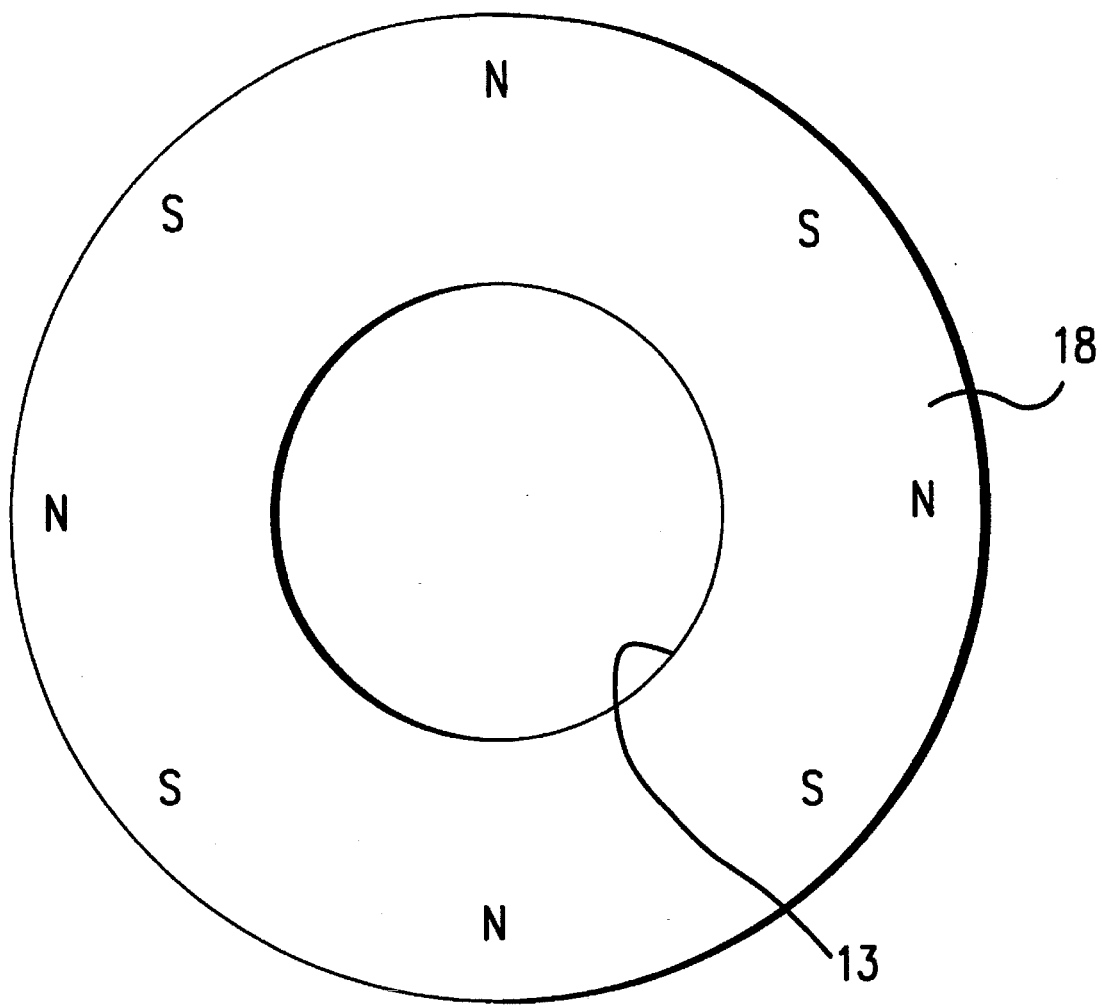
FIG. 6 is a plan view showing another embodiment of the magnetic field generating source.

In addition, as shown in FIG. 6, a magnetic field generating source 10 may be configured by an annular permanent magnet 18 which is magnetized along an outer peripheral surface of the magnet.

Figure 7:
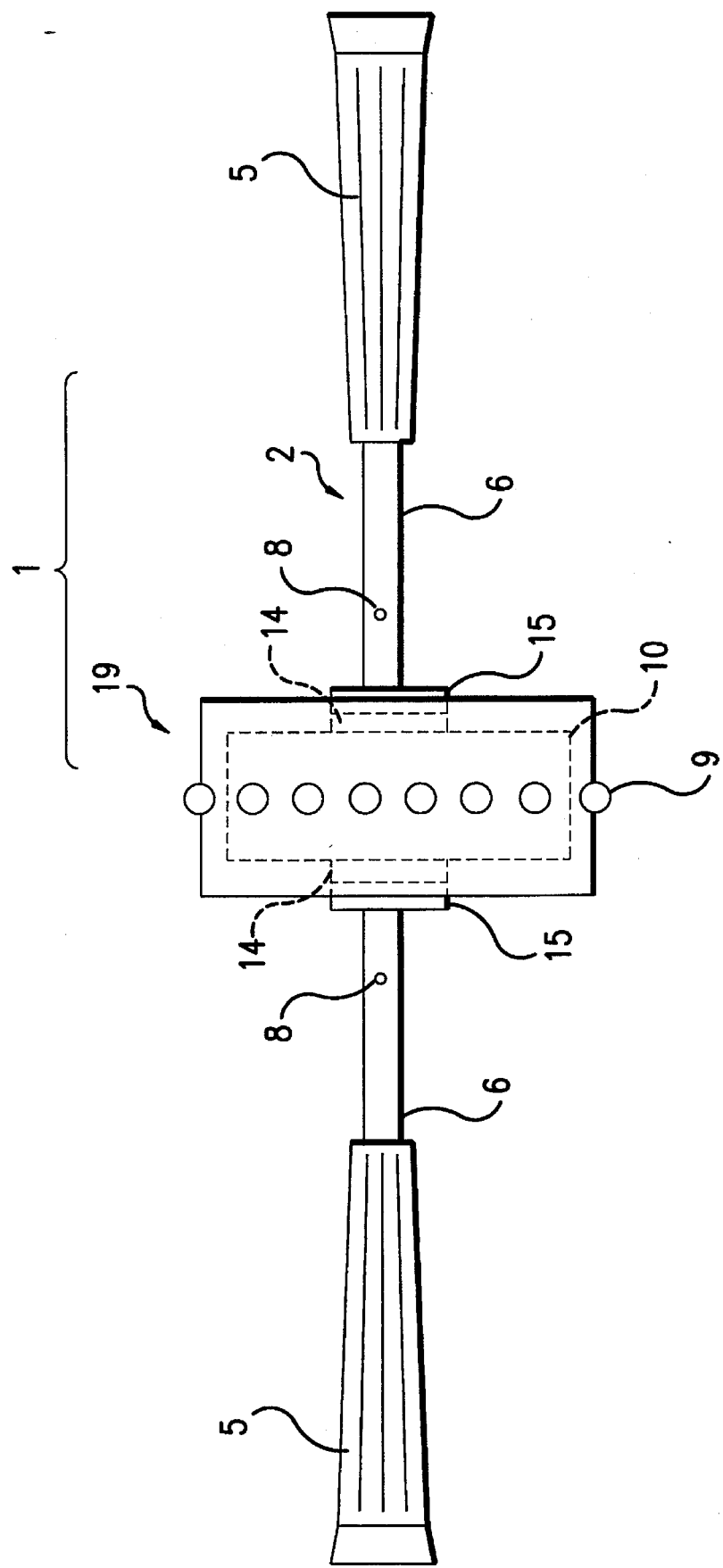
FIG. 7 is a front view showing an appearance of the roller therapeutic appliance of the second embodiment of the present invention.

FIG. 7 shows an appearance of a roller therapeutic appliance 1 of the second embodiment of the invention.

The appliance of this embodiment has a disk-shaped pressure roller 19, and one magnetic field generating source 10 is embedded, below the row of the small protrusions 9, in the pressure roller 19.

In addition, other structures of this embodiment which correspond to that of the first embodiment are given the same reference numeral and thus explanations on them are omitted.

Figure 8:
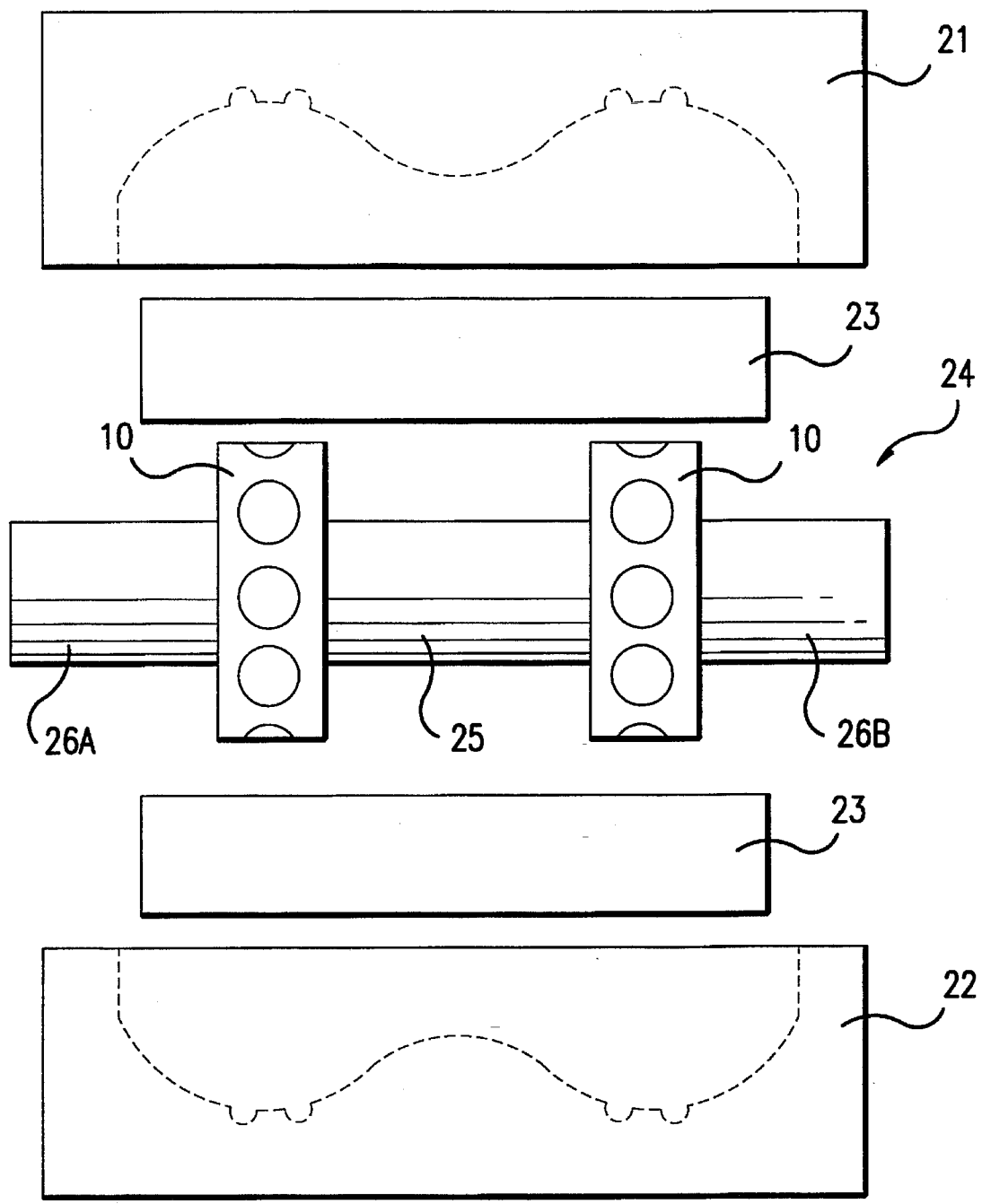
FIG. 8 is an illustration showing the method of fabricating the roller therapeutic appliance of the first embodiment.
Figure 9:
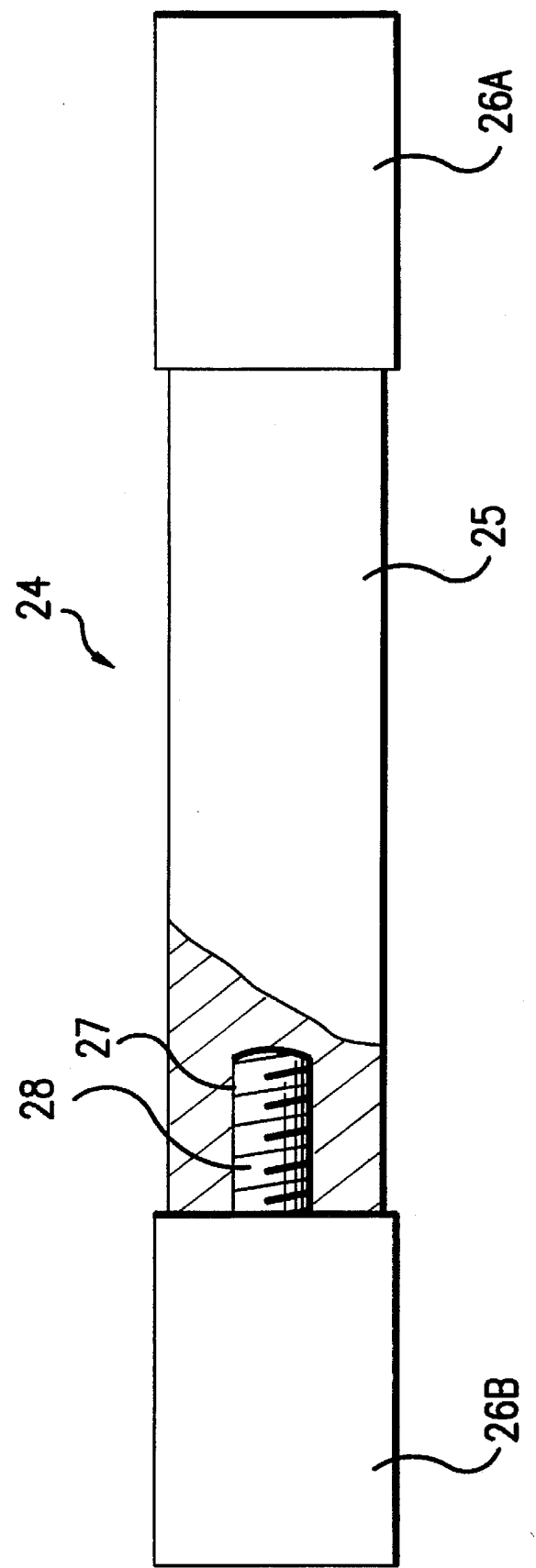
FIG. 9 is a partially broken front view showing a rod-shaped jig.

A roller therapeutic appliance 1 according to the above-mentioned first embodiment is fabricated by serially performing the steps described in detail as follows, and FIG. 8 schematically shows the process of molding the pressure roller 3.

In the first step as a preliminary stage, two of the magnetic field generating source 10, 10 which are to be embedded in the pressure roller 3 and a rod-shaped Jig 24 shown in FIG.

9 are prepared, and the jig 24 is inserted into the inner holes 13, 13 of the magnetic field generating sources 10, 10, and the magnetic field generating sources 10, 10 are supported on the jig 24, with a predetermined spacing between them.

Said rod-shaped jig 24 is made somewhat longer than the pressure roller 3 and configured of an axis 25 which has the same outer diameter as the inner diameter of the inner hole 13 of the magnetic field generating source 10 and block portions 26A, 26B which are positioned at both ends of the axis 25 and have a somewhat larger outer diameter than that of the axis 25. One block portion 26A is integrally formed with the axis 25, while the other block portion 26B is detachably fixed to the axis 25. The block portion 26B is protrusively provided with a screw portion 28 that engages with a tapped hole 27 formed at an end of the axis 25. The axis 25 is formed into a certain length corresponding to a spacing between the two embedded magnetic field generating sources 10, 10.

In this process, one block portion 26B is separated from the axis 25, and the axis 25 is inserted into the inner holes 13, 13 of the magnetic field generating sources 10, 10, thereafter the block portion 26B is attached to the axis 25. Thereby, the magnetic field generating sources 10, 10 contact the block portions 26A, 26B to be blocked.

In the next step, the pressure roller 3 embedding the magnetic field generating sources 10, 10 are molded by using a pair of an upper die 21 and a lower die 22 shown in FIG. 8.

Each dies 21 and 22 has a mold cavity conforming to the outer shape of the pressure roller 3. The magnetic field generating sources 10, 10 in a state of being supported on the jig 24 and rubber plates 23, 23 are introduced between the dies, thereafter the upper die 21 and the lower die 22 are closed and pressurized in a state of heat application.

Thereby the rubber plates 23, 23 are deformed under heating and formed Into the shape of the pressure roller 3 by the upper die 21 and the lower die 22, and thus the magnetic field generating sources 10, 10 are embedded in the pressure roller 3.

In the third step, the jig 24 is pulled out from the molded pressure roller 3.

First, the block portion 26B, of the jig 24, projecting from one end of the pressure roller 3 is removed and separated from the axis 25, thereafter the axis 25 is pulled out from the other end of the pressure roller 3 by pulling the block portion 26A. A space formed in the pressure roller 3 after pulling out the jig 24 is the hollow hole 11.

In the last step, the non-skid rings 14, 14 and the bearing 15, 15 are fitted into both the end portions 11b, 11b of the hollow hole 11 of the pressure roller 3, and the metal rod 4 of the operation axis 2 is inserted into said bearings 15, 15 to rotatably support the pressure roller 3. Thereafter the metal pipes 6, 6 are respectively fitted to the both end portions of the metal rod 4 which project from the pressure roller 3. And the end faces of the metal pipes 6, 6 are made to contact with the bearings 15, 15, then the metal pipes 6, 6 and the metal rod 4 are fixed by the rivets 8, 8.

Figure 10:
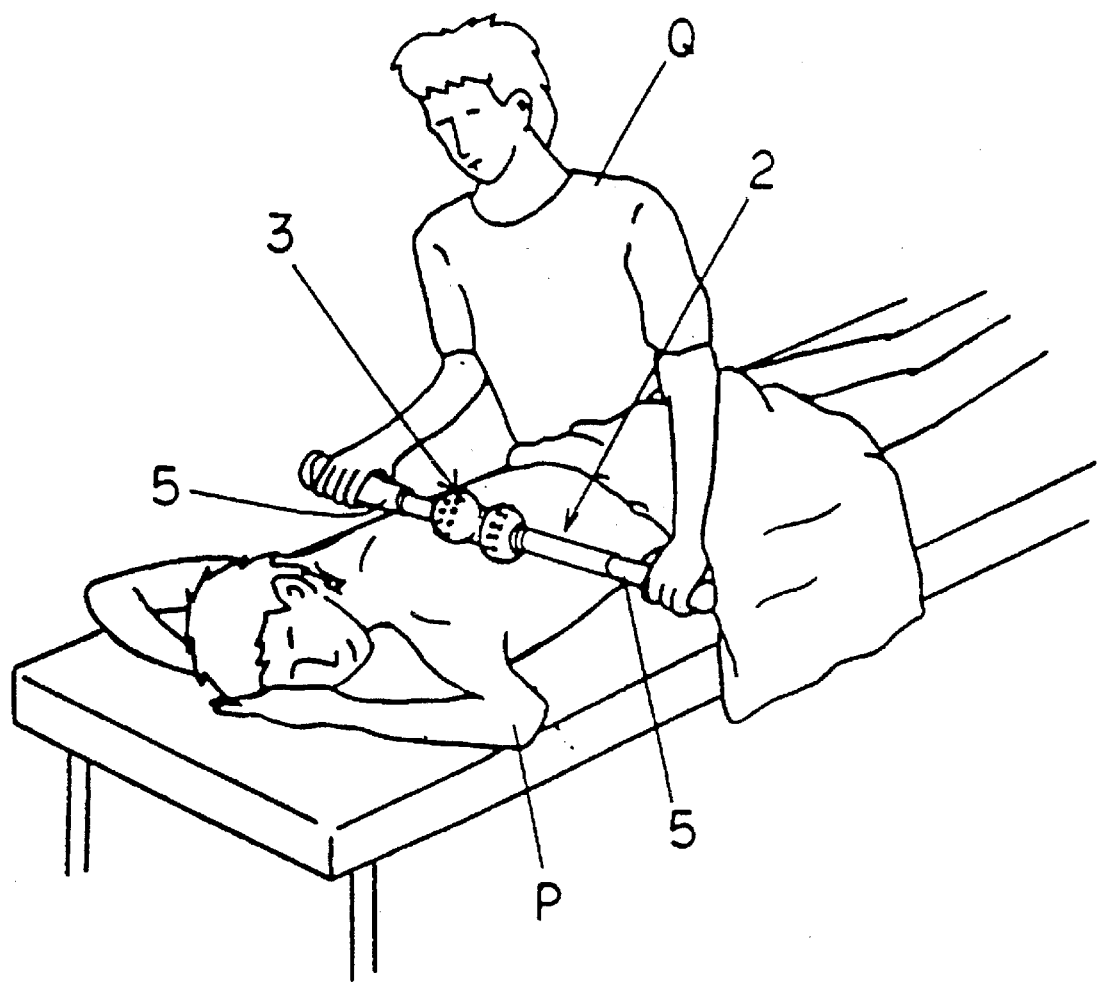
FIG. 10 is an illustration showing a method of using a roller therapeutic appliance of the first embodiment.

FIG. 10 shows a method of using the roller therapeutic appliance 1 according to the first embodiment.

First, a patient P is kept to lie facing downward, and a person Q in charge of medical treatment grasps the grips 5, 5 at both ends of the operation axis 2 and applys the presses the pressure roller 3 on the patient P's back or the like part. Then, the contracted center part 3c of the pressure roller 3 comes just above the patient P's spine, thus at this condition, person Q applies the operation axis 2 taking advantage of his weight on for exerting pressure by the pressure roller 3 and rolls the roller 3 along patient P's spine. Due to this pressure, patient P's muscles along his spine are softened, and the small protrusions 9 on the pressure roller 3 press and stimulate patient P's physical points, which can give an excellent massage effect. Furthermore, magnetic lines of force generated by the magnetic field generating sources 10 act on the human body, which can give a magnetic therapeutic effect.

Moreover, it is possible for patient himself to grasp the grips 5, 5 and press the pressure roller 3 on his diseased part and roll the roller for massaging.

In addition, the roller therapeutic appliance 1 according to the second embodiment is fabricated in the same way as the first embodiment and is used in the same manner as the roller massage appliance 1 of the first embodiment.

What is claimed is:

1. A method of fabricating a roller therapeutic appliance comprising the steps of:

inserting a rod-shaped jig into an inner hole of an annular magnetic field generating source on the jig;

introducing the annular magnetic field generating source supported on said jig along with an elastic material between molds;

pressurizing and applying heat to said molds and thereby molding a pressure roller embedding said magnetic field generating source;

pulling out said jig from the molded pressure roller;

fitting bearings into an inner hole of the pressure roller; and inserting a rod having an operation axis into the bearings, and thereby rotatably supporting the pressure roller on said rod for rotation about said operation axis.

* * * * *